(12) United States Patent
Cisko, Jr. et al.

(10) Patent No.: US 11,234,856 B2
(45) Date of Patent: Feb. 1, 2022

(54) OSTOMY BELT SYSTEM

(71) Applicant: Hollister Incorporated, Libertyville, IL (US)

(72) Inventors: George J. Cisko, Jr., Spring Grove, IL (US); Brock E. Masters, Des Plaines, IL (US); Ryan S. Park, Northbrook, IL (US); Peter L. Visconti, Gurnee, IL (US); Brian T. Leadingham, Pleasant Prairie, WI (US); Patrick C. Tetzlaff, Caledonia, WI (US)

(73) Assignee: Hollister Incorporated, Libertyville, IL (US)

(*) Notice: Subject to any disclaimer, the term of this patent is extended or adjusted under 35 U.S.C. 154(b) by 598 days.

(21) Appl. No.: 16/086,544

(22) PCT Filed: Apr. 25, 2017

(86) PCT No.: PCT/US2017/029356
§ 371 (c)(1),
(2) Date: Sep. 19, 2018

(87) PCT Pub. No.: WO2017/189544
PCT Pub. Date: Nov. 2, 2017

(65) Prior Publication Data
US 2019/0083295 A1    Mar. 21, 2019

Related U.S. Application Data

(60) Provisional application No. 62/329,706, filed on Apr. 29, 2016.

(51) Int. Cl.
*A61F 5/449* (2006.01)
*A61F 5/448* (2006.01)

(52) U.S. Cl.
CPC .............. *A61F 5/449* (2013.01); *A61F 5/448* (2013.01)

(58) Field of Classification Search
CPC .. A61F 5/449; A61F 5/448; A61F 2005/4486; A61F 2005/4495
See application file for complete search history.

(56) References Cited

U.S. PATENT DOCUMENTS 1,355,766 A     10/1920 McGrory
2,837,094 A *    6/1958 Cowles ................... A61F 5/445
                                                    604/338

(Continued)

FOREIGN PATENT DOCUMENTS

CA      2312684 A1 * 12/2000  ............. A61F 5/449
FR      2947445 A3 *  1/2011  ............... A61F 5/28

(Continued)

OTHER PUBLICATIONS

International Preliminary Report on Patentability and Written Opinion issued by IB in connection with PCT/US2017/029356 dated Oct. 30, 2018.

*Primary Examiner* — Adam Marcetich
(74) *Attorney, Agent, or Firm* — Levenfeld Pearlstein, LLC

(57) ABSTRACT

An ostomy belt system includes an ostomy belt having a strip of material and a belt coupling element, and an ostomy pouch having and outer wall defining an inner volume, and a pouch coupling section configured for releasable engagement with the belt coupling element. One or both of the belt coupling element and the pouch coupling section is configured to bend or flex at a predetermined location.

12 Claims, 3 Drawing Sheets

(56) References Cited

U.S. PATENT DOCUMENTS

| | | | |
|---|---|---|---|
| 3,074,404 A | 1/1963 | Robinson | |
| 3,076,458 A | 2/1963 | Mason | |
| 3,602,227 A * | 8/1971 | Andrew | A61M 25/02 |
| | | | 128/207.17 |
| 3,760,811 A * | 9/1973 | Andrew | A61M 25/02 |
| | | | 128/207.17 |
| 4,471,776 A * | 9/1984 | Cox | A61M 16/04 |
| | | | 128/207.15 |
| 4,612,230 A * | 9/1986 | Liland | A61B 17/085 |
| | | | 428/167 |
| 5,026,352 A * | 6/1991 | Anderson | A61M 16/0488 |
| | | | 128/207.17 |
| 5,026,360 A * | 6/1991 | Johnsen | A61F 5/448 |
| | | | 292/256.69 |
| 5,026,361 A * | 6/1991 | Matysiak | A61F 5/445 |
| | | | 604/338 |
| 5,320,097 A * | 6/1994 | Clemens | A61M 16/0488 |
| | | | 128/207.17 |
| 5,626,570 A * | 5/1997 | Gallo | A61F 5/449 |
| | | | 2/49.2 |
| 5,704,905 A * | 1/1998 | Jensen | A61F 13/0259 |
| | | | 602/42 |
| 5,811,116 A * | 9/1998 | Gilman | A61F 5/443 |
| | | | 424/443 |
| 2006/0064049 A1 * | 3/2006 | Marcussen | A61F 13/025 |
| | | | 602/42 |
| 2007/0068533 A1 * | 3/2007 | Bierman | A61M 16/0497 |
| | | | 128/207.17 |
| 2008/0154169 A1 * | 6/2008 | Kase | A61F 13/023 |
| | | | 602/55 |
| 2009/0118687 A1 * | 5/2009 | Kristensen | A61F 5/448 |
| | | | 604/342 |
| 2010/0168693 A1 * | 7/2010 | Edvardsen | A61F 5/443 |
| | | | 604/355 |
| 2010/0191202 A1 * | 7/2010 | Hogard | A61F 5/448 |
| | | | 604/342 |
| 2010/0324511 A1 * | 12/2010 | Dove | A61F 5/445 |
| | | | 604/342 |
| 2012/0220967 A1 * | 8/2012 | Lundholt | A61F 5/448 |
| | | | 604/342 |
| 2013/0226116 A1 * | 8/2013 | Edvardsen | A61F 5/445 |
| | | | 604/338 |
| 2014/0276501 A1 * | 9/2014 | Cisko | A61F 5/455 |
| | | | 604/344 |
| 2015/0126816 A1 * | 5/2015 | O'Prey | A61B 17/3431 |
| | | | 600/204 |
| 2015/0257922 A1 * | 9/2015 | Schertiger | A61F 5/448 |
| | | | 604/344 |
| 2017/0143535 A1 * | 5/2017 | Praame | A61F 5/445 |
| 2017/0181885 A1 * | 6/2017 | Galindo | A61F 5/449 |
| 2018/0055679 A1 * | 3/2018 | Hewitt | A61F 5/443 |

FOREIGN PATENT DOCUMENTS

| | | |
|---|---|---|
| JP | H9122163 A | 5/1997 |
| JP | 2005278744 A | 10/2005 |
| JP | 3153484 U | 9/2009 |
| KR | 20100006427 U * | 6/2010 |
| WO | 2015171173 A1 | 11/2015 |

* cited by examiner

OSTOMY BELT SYSTEM

This is a National Stage Application of International Patent Application No. PCT/US2017/029356, filed Apr. 25, 2017, which claims the benefit of and priority to U.S. Provisional Application No. 62/329,706, filed Apr. 29, 2016, the entirety of which are incorporated fully herein by reference.

BACKGROUND

The following description relates to an ostomy appliance, and in particular, an ostomy support belt system for supporting an ostomy pouch on a person having an ostomy.

An ostomy appliance or system is a medical device or prosthetic that provides a means for collecting waste from a stoma typically created as a result of a surgical procedure to divert a portion of the colon or small intestine. One type of ostomy appliance is an ostomy pouch system that may be attached to the ostomate (person having the ostomy), around the stoma or the peristomal region.

Ostomy pouches can be connected to the ostomate in a variety of ways. In one arrangement, a faceplate includes a body-facing side, a pouch-facing side, an opening and a faceplate coupling section. The body-facing side is adhered to the ostomate at a peristomal area. The opening is configured to receive the stoma therethrough. The coupling section is formed on the pouch-facing side. The ostomy pouch includes an inlet and a pouch coupling section around the inlet. The pouch coupling section is coupled to the faceplate coupling section such that the opening and the pouch inlet are aligned. In other configurations, the faceplate and ostomy pouch may be integrally formed as a one-piece system. In both configurations, bodily waste may be received from the stoma into the pouch.

Another arrangement for connecting an ostomy pouch to an ostomate includes an ostomy belt system. An ostomy belt typically extends around the ostomate's abdomen or waist and includes hooks or clasps at opposite ends of the belt. The ostomy pouch includes a pouch coupling ring having opposed belt tabs, typically disposed about 180 degrees apart on the ring. The hooks or clasps are configured for mating engagement with respective belt tabs. The ostomy pouch typically includes a sealing part extending from a body-facing pouch wall to adhesively bond to the ostomate's skin. Thus, the belt is connected to the pouch coupling ring at a region between the ostomy pouch and the sealing section. The ostomy belt partially supports the ostomy pouch and any contents thereof.

However, in the ostomy belt systems above, pouch coupling rings on the ostomy pouch are relatively inflexible. As a result, a point of contact of the pouch coupling ring to the ostomate's skin in the peristomal region may cause discomfort, especially where the stoma is recessed or during movement of the ostomate. In addition, because the pouch coupling ring does not move with a changing contour of the ostomate's abdomen (for example, during movement of the ostomate), the pouch coupling ring may pull against a sealing adhesive and could weaken or break the seal at the ostomate's skin. Further, the coupling ring of the ostomy pouch acts as a support structure around the inlet opening of the ostomy pouch. However, making the ostomy pouch with the coupling ring requires additional manufacturing steps, e.g., heat sealing, that may be costly or time consuming. Further still, an ostomate or caretaker may find it difficult to engage the clasps or hooks of an ostomy belt with the belt tabs of the pouch coupling ring to connect the ostomy belt to the ostomy pouch.

Accordingly, it is desirable to provide an ostomy belt system having a flexible coupling attachment at the peristomal region of the ostomate that is convenient to use and/or reduces complexity and parts.

SUMMARY

In one embodiment, there is provided an ostomy belt system including an ostomy belt having a strip of material and a belt coupling element, and an ostomy pouch having and outer wall defining an inner volume and a pouch coupling section configured for releasable engagement with the belt coupling element. One or both of the belt coupling element and the pouch coupling section is configured to bend or flex at a predetermined location.

According to another embodiment, there is provided an ostomy belt having a strip of material including a first end and a second end, a first coupling element secured to the first end, a second coupling element secured to the second end configured for releasable engagement with the first coupling element, and one or more flexible sections formed on each of the first and second coupling elements to allow for flexing of each coupling element at one or more predetermined locations.

According to still another embodiment, there is provided an ostomy pouch including a proximal side having an inlet opening, a distal side opposite to the proximal side, an interior volume defined between the proximal side and the distal side, and a pouch coupling ring disposed on an exterior side of the proximal side and positioned about the inlet opening. The pouch coupling ring includes one or more pouch fasteners configured for engagement with an ostomy belt and one or more flexible sections to allow for flexing at one or more predetermined locations.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
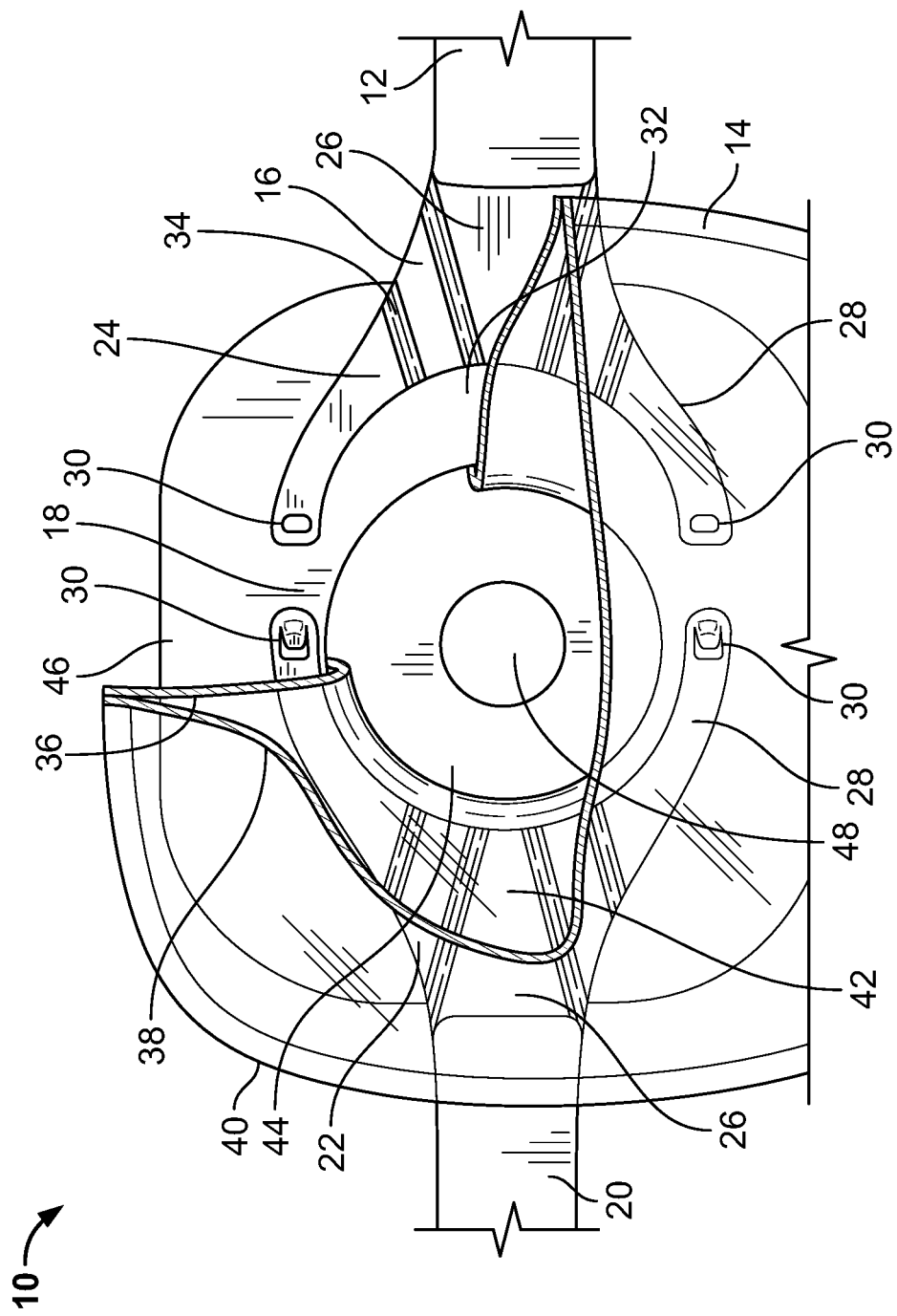
FIG. 1 is a transparent plan view of an ostomy belt system according to an embodiment described herein.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 3:
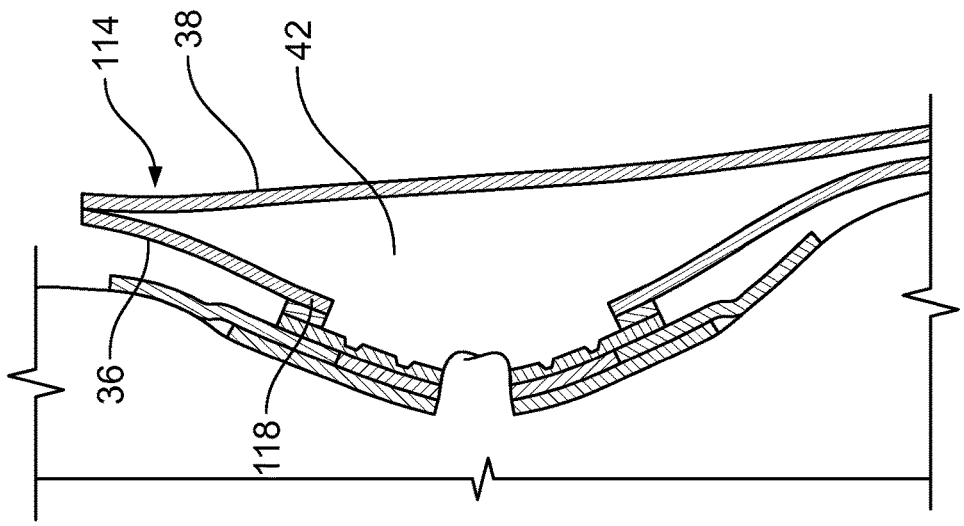
FIG. 3 is a cross-sectional view of the ostomy belt system of FIG. 2.
Figure 2:
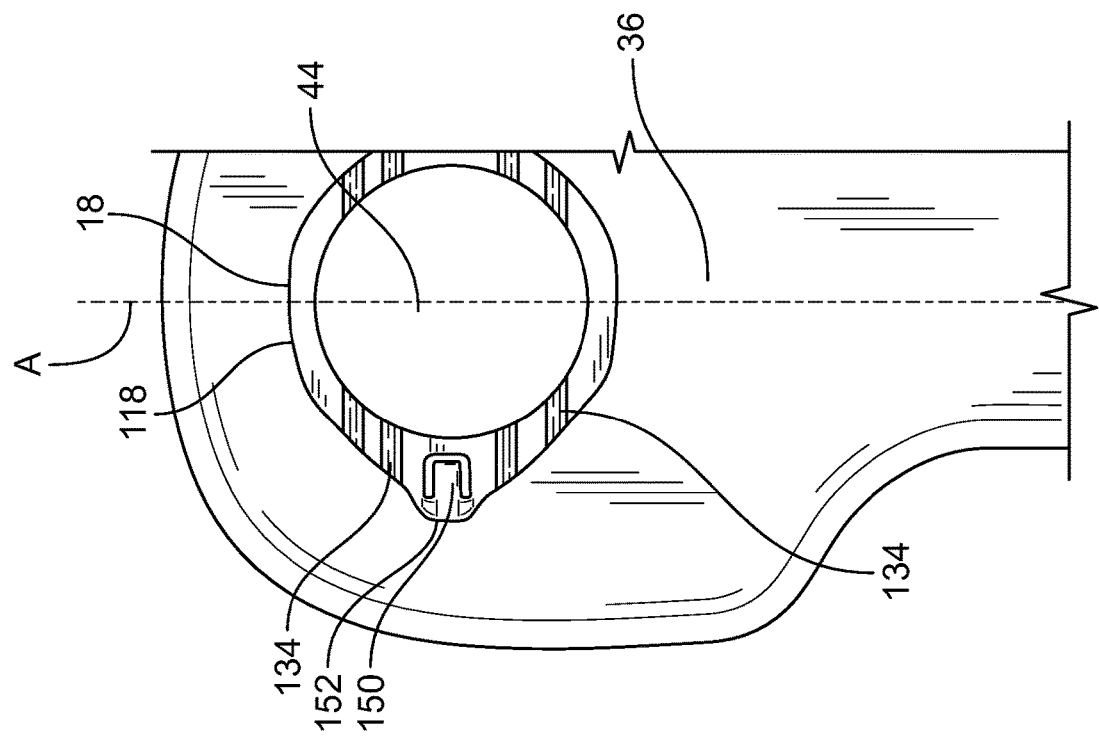
FIG. 2 is a plan view of an ostomy pouch of an ostomy belt system according to another embodiment described herein.

Referring generally to FIGS. 1-3, an ostomy belt system 10 in accordance with the embodiments described herein includes an ostomy belt 12 and an ostomy pouch 14. The ostomy belt 12 includes a belt coupling element 16 and the ostomy pouch 14 includes a pouch coupling section 18 configured for cooperating, releasable engagement with the belt coupling element 16. In one embodiment, one, or both of the belt coupling element 16 and the pouch coupling section 18 may bend or flex with movement of the ostomate's abdomen. To this end, one or both of the belt coupling element 16 and the pouch coupling section 18 may include one or more flexible sections as described below.

Figure 4:
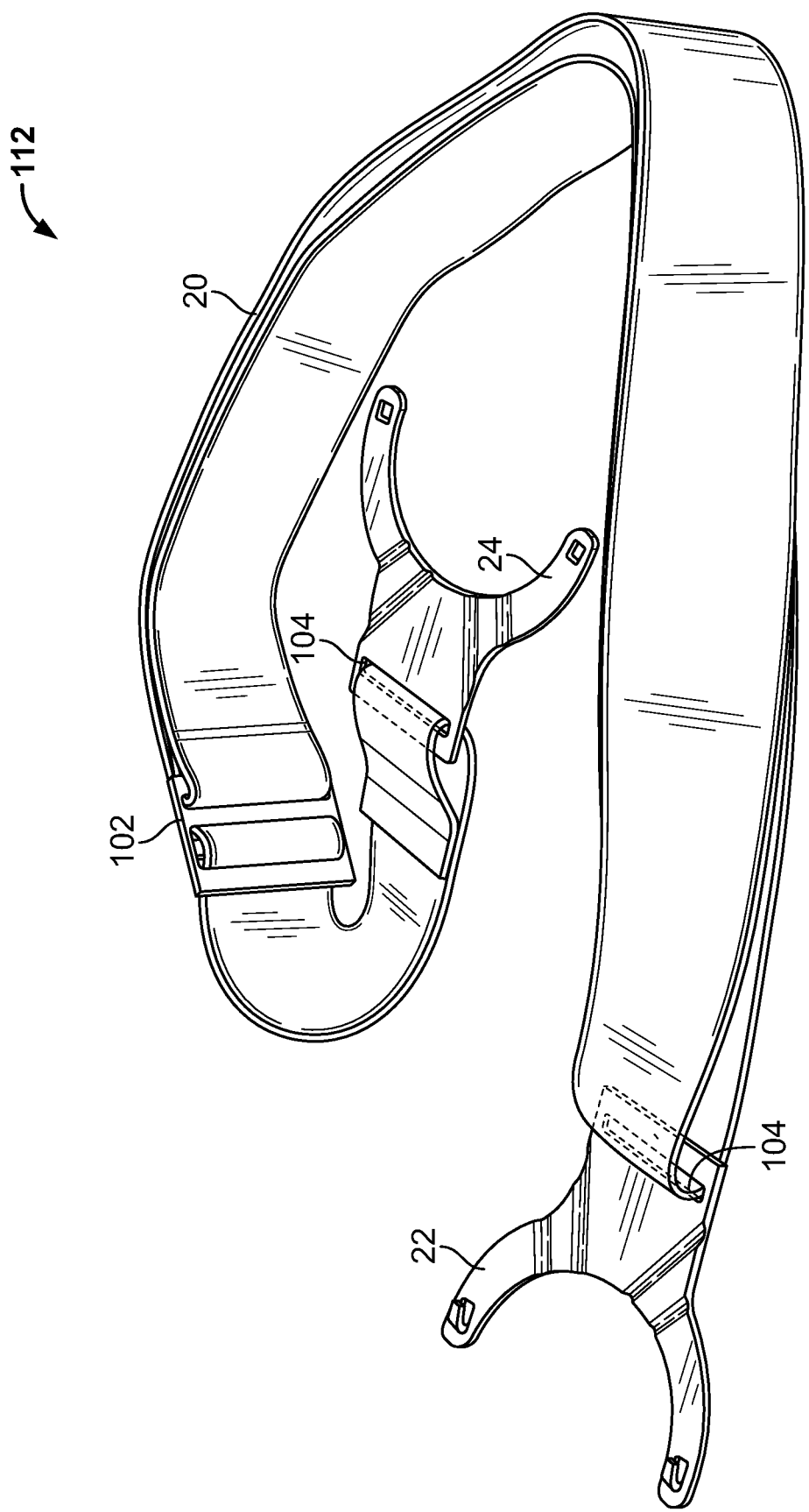
FIG. 4 is a perspective view of an ostomy belt according to an embodiment.

FIG. 1 is a transparent plan view of the ostomy belt system 10 according to one embodiment described herein. The ostomy belt 12 includes a strip of material 20 and the belt coupling element 16 is disposed at one or both ends of the strip of material 20. The strip of material 20 may be elasticated or include elastic sections. In one embodiment, the belt coupling element 16 includes a first coupling element 22 and a second coupling element 24 disposed at respective ends of the strip of material 20. In another embodiment, the ostomy belt 112 may be configured as an adjustable belt including a sliding buckle 102 to accommodate different waist sizes as shown in FIG. 4. In such an embodiment, the first and second coupling elements 22, 24 may include an opening 104 for receiving the strip of material 20.

Each coupling element 22, 24 generally includes a base 26 secured to the strip of material 20 and a fastening portion 28 extending from the base 26. The base 26 and the fastening portion 28 may be integrally formed as one piece. The fastening portion 28 of the first coupling element 22 is configured to releasably engage the fastening portion 28 of the second coupling element. To this end, each fastening portion 28 includes one or more fasteners 30 configured for releasable, mating engagement with respective corresponding fasteners 30 on the other fastening portion 28.

In one embodiment, the fasteners 30 may be, for example, snap fit, friction fit, interference fit, positive interlocking or other suitable types of fasteners. For example, a fastener on the first coupling element 22 may be formed as a hook or tab, and the corresponding fastener on the second coupling element 24 may be an aperture or recess configured to receive the hook or tab. Other suitable fasteners include, but are not limited to, clasps, clips, hook-and-loop fasteners, adhesives and the like.

In one embodiment, the first and second coupling elements 22, 24 are configured to engage one another to form a closed or substantially closed loop having a central opening 32. In one embodiment, the fastening portion 28 of each of the first and second coupling elements 22, 24 may be an open, curved section, for example, substantially semi-circular, such that when connected to one another, the first and second coupling elements 22, 24 form a substantially circular central opening 32. However, the present disclosure is not limited to this example and other shapes for the central opening 32 are envisioned, including, but not limited to, oval, elliptical and other substantially closed loop shapes. Additionally, in one embodiment, an outer periphery of the fastening portions 28 is substantially rounded or curved so as to be free of angles that may protrude into the ostomate's skin.

In the embodiments above, the fasteners 30 may be disposed on substantially opposite ends of the each fastening portion 28. For example, a lower end of each fastening portion 28 may include corresponding fasteners 30 configured for releasable engagement with one another, and an upper end of each fastening portion 28 may include corresponding fasteners 30 configured for releasable engagement with one another.

In addition, the fasteners 30 disposed at different positions of each fastening portion 28 may be implemented as different types of fasteners. For example, in one embodiment, the corresponding fasteners 30 at one of the upper end and the lower end may, when engaged, form a pivotable or rotatable connection such that the corresponding fasteners 30 at the other of the upper end and lower end may rotate toward one another for engagement or away from one another when disengaged.

The first and second coupling elements 22, 24 may also include one or more flexible sections 34 configured to allow each coupling element 22, 24 to bend or flex with movement of the ostomate. In addition, the one or more flexible sections 34 may allow the belt coupling element 16 to substantially conform to the contour of a concave peristomal region around a recessed stoma. In one embodiment, the one or more flexible sections 34 are formed by areas or lines of reduced material thickness in the fastening portion 28 to form a living hinge. In another embodiment, the one or more flexible sections 34 may be formed by progressively varying a thickness or profile of the coupling elements 22, 24. For example, in one embodiment, upper and lower ends of each coupling element 22, 24 may be formed having a first thickness, and a central area between the upper and lower ends may have a second thickness less than the first thickness. Moving from an upper or lower end to the central area, the thickness may reduce gradually or step wise. In another configuration, the central area may have a thickness greater than the upper and lower ends.

In another embodiment, the one or more flexible sections 34 may be formed by using a different, more flexible material. For example, each coupling element 22, 24 may be formed in a two-shot molding process where different materials having different properties are used. In one embodiment, the flexible section(s) 34 may be molded from a suitably flexible material, such as thermoplastic elastomer (TPE), polyethylene and the like, while adjacent, relatively less flexible sections of each coupling element 22, 24 may be molded from a relatively stiffer material, such as polypropylene and the like. Other suitable materials having different relative flexibility or stiffness properties may be used as well.

It is understood that individual flexible sections may be formed according to one or more of the techniques above. For example, a flexible section may be formed from two materials having different flexibility characteristics or properties together with a varying material thickness or profile. Further, it is understood that different flexible sections formed on the same part may be formed according to different techniques described above. For example, one flexible section may be formed from two materials having different flexibility characteristics or properties while another flexible section may be formed with a reduced material thickness.

The one or more flexible sections 34 may extend in different orientations and/or be differently shaped than one another to obtain desired flexibility characteristics. In addition, coupling element 22, 24 may include different flexible sections 34 formed using one or more of the techniques described above.

The first and second coupling elements 22, 24 may be moved toward one another such that the corresponding fasteners 30 engage to secure the coupling elements 22, 24 to one another. In one embodiment, an elasticity in the strip of material 20, urging the coupling elements 22, 24 away from one another, may hold the corresponding fasteners 30 in engagement with one another. The coupling elements 22, 24 may be moved toward one another to overcome the elasticity and disengage the corresponding fasteners 30. Alternatively, or in addition, the corresponding fasteners 30 may be released by applying a pinching or squeezing force to the fasteners 30, for example, to release a tab or hook from a recess. In another embodiment, a pulling force applied to the corresponding fasteners 30 may serve to disengage the fasteners 30 from one another.

In the embodiments above, with the coupling elements 22, 24 engaged with one another, the belt coupling element 16 may substantially form a belt coupling ring configured to fit around and engage a portion of the ostomy pouch 14, thereby securing the ostomy pouch 14 to the belt 12. The coupling element 16 provides structural support and/or reinforcement around an inlet in the ostomy pouch 14. Thus, with the belt coupling element 16 in the embodiments above, a known pouch coupling ring may be omitted from the ostomy belt system 10. In addition, with the corresponding fasteners 30 described in the embodiments above, an ostomate or caretaker may be able to more easily secure the ostomy belt to the ostomy pouch. This configuration may also be beneficial to those users with limited dexterity. Further still, one or more flexible sections 34 may allow for the coupling element 16 to bend or flex with movement of the wearer and conform to concave peristomal regions, improving comfort and limiting pulling forces that may adversely affect seal quality against the wearer's skin.

Still referring to FIG. 1, the ostomy pouch 14 may be formed having an outer wall with a proximal side 36 and a distal side 38 opposite to the proximal side 36. The ostomy pouch 14 may be a one-piece ostomy pouch where the proximal and distal sides 36, 38 are formed as a single continuous piece. Alternatively, the ostomy pouch 14 may be formed from two or more pieces. For example, the proximal side 36 may be a proximal side wall 36 and the distal side 38 may be a distal side wall 38. The proximal side wall 36 and distal side wall 38 may be connected to one another about their respective peripheries to form an ostomy pouch periphery 40. The proximal and distal side walls 36, 38 may be connected, for example, by heat sealing or other similar, known methods.

The proximal and distal sides 36, 38 define an interior volume 42 therebetween configured to collect and store bodily waste received from a stoma. To this end, the proximal side 36 includes an inlet opening 44 through which the bodily waste may be received. The pouch coupling section 18 is disposed adjacent to and around the inlet opening 44 on an exterior portion of the proximal side 36, i.e., not in the interior volume 42. A barrier 46 extends from the inlet opening 44, and may be formed as, for example, a faceplate. The barrier 46 includes an adhesive on a body-facing side for bonding to the ostomate's abdomen in the peristomal region. The barrier 46 also includes an inlet 48 generally aligned within the inlet opening 44 through which bodily waste may be received. The pouch coupling section 18 is disposed between the proximal side 36 and the barrier 46.

In the embodiments above, the belt coupling element 16 may be disposed between the barrier 46 and the proximal side 36 of the ostomy pouch 14 at the pouch coupling section 18. The first and second coupling elements 22, 24 substantially surround the inlet opening 44 of the ostomy pouch 14, and the central opening 32 of the belt coupling element 16 has an inner diameter approximately equal too, or slightly larger than an outer diameter of the pouch inlet opening 44.

The belt coupling element 16 may be urged against the ostomate's body by way of an elastic force applied by the strip of the material 20.

FIG. 2 is a plan view of an ostomy pouch 114 used in an ostomy belt system according to another embodiment described herein and FIG. 3 is a cross-sectional view of the ostomy belt system of FIG. 2. In the following embodiments, features similar or identical to those above will be referred to using the same terminology and identified with like reference characters. Referring to FIGS. 2 and 3, in one embodiment, ostomy pouch 114 may be formed substantially the same as the ostomy pouch 14 described in the embodiments above. However, as shown in FIGS. 2 and 3, the pouch coupling section 18 of the ostomy pouch 114 may be formed as a pouch coupling ring 118 positioned on the proximal side 36, i.e., the body-facing side, of the ostomy pouch 114. The pouch coupling ring 118 substantially or completely surrounds the inlet opening 44 of the ostomy pouch 114 and is configured for releasable, mating engagement with a belt fastener of an ostomy belt.

In one embodiment, the pouch coupling ring 118 includes one or more pouch fasteners 150 configured for releasable, mating engagement with a corresponding fastener of the ostomy belt. Preferably, the one or more pouch fasteners 150 are formed as two pouch fasteners 150 positioned substantially diametrically opposite from one another. However, the present disclosure is not limited to this configuration, and the number of pouch fasteners 150 may vary. In one embodiment, each pouch fastener 150 may be disposed on a respective fastening tab 152. The pouch fasteners 150 are configured for releasable engagement with a corresponding belt fastener of the ostomy belt.

In one embodiment, the pouch fasteners 150 and the corresponding belt fasteners may be, for example, snap fit, friction fit, interference fit, positive interlocking or other suitable types of fasteners. For example, the pouch fastener 150 may be formed as a hook or tab, and the corresponding belt fastener may be an aperture or recess configured to receive the hook or tab, or vice versa. Other suitable fasteners include, but are not limited to, clasps, clips, hook-and-loop fasteners, adhesives and the like.

The pouch coupling ring 118 may also include one or more flexible sections 134. The one or more flexible sections 134 of the pouch coupling ring 118 may be formed similarly to the one or more flexible sections 34 of the first and second coupling elements 22, 24 described above. For example, the one or more flexible sections 134 of the pouch coupling ring 118 may be formed by areas or lines of reduced material thickness (e.g., a living hinge), a progressively varying thickness, or different materials having different flexibility or stiffness properties molded in a two-shot injection molding process, or a combination thereof.

In one embodiment, the one or more flexible sections 134 may be formed as a plurality of spaced apart lines extending across a width of the pouch coupling ring 118. The spaced apart lines may be substantially parallel to one another and may be formed substantially in a mirrored relationship across a vertical axis 'A'. However, the present disclosure is not limited to this configuration Accordingly, the pouch coupling ring 118 may flex or bend at predetermined locations, i.e., at the one or more flexible sections 134, so as to accommodate movement of the ostomate's body The flexibility of the pouch coupling section ring 118 is intended to substantially reduce or prevent point contact in the peristomal region. In addition, the flexibility of the pouch coupling ring 118 allows for the pouch coupling ring 118 to substantially match a contour of the peristomal region, for example, around a recessed stoma. Thus, in addition to the envisioned comfort benefits, the pouch coupling ring 118 may apply less of a pulling force to an adhesive seal against the ostomate's skin, vis-à-vis a known flat coupling ring, and thus, may better maintain seal integrity.

Elements from different embodiments above may be used together. For example, the belt coupling element 16 may releasably and matingly engage the pouch coupling ring 118. That is, in one embodiment, the belt coupling element 16 may be formed as a known hook or clasp for releasable engagement with the pouch fasteners 150 of the pouch coupling ring 118. Additionally, in one embodiment, the belt coupling element and pouch coupling section may each include one or more flexible sections configured to allow bending or flexing at predetermined locations.

It is understood that the relative directions described above, e.g., "upward," "downward," "upper," "lower," "above," "below," are used for illustrative purposes only and may change depending on an orientation of the ostomy pouch and/or the patient. Accordingly, this terminology is non-limiting in nature.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy belt system comprising:
   an ostomy belt having a strip of material and a belt coupling element; and
   an ostomy pouch having an outer wall defining an inner volume, and a pouch coupling section configured for releasable engagement with the belt coupling element, wherein the belt coupling element includes a plurality of flexible sections formed by one or more of areas or lines of a reduced material thickness, changes in material profile, and two materials having different flexibility properties, which are configured to allow the belt coupling element to bend or flex with movement of a user and to conform to a contour of a peristomal region of the user, wherein the belt coupling element includes a first coupling element and a second coupling element configured to engage one another to form a closed loop having a central opening.

2. The ostomy belt system of claim 1, wherein the first coupling element and the second coupling element are secured to the strip of material, wherein the first coupling element includes one or more fasteners and the second coupling element includes one or more corresponding fasteners configured to releasably engage respective fasteners of the first coupling element.

3. The ostomy belt system of claim 2, wherein the first coupling element and second coupling element each includes a base secured to the strip of material and a fastening portion extending from the base.

4. The ostomy belt system of claim 3, wherein the base includes an opening for receiving the strip of material, wherein the ostomy belt is configured as an adjustable belt including a sliding buckle.

5. The ostomy belt system of claim 3, wherein the respective fastening portions form open, curved sections.

6. The ostomy belt system of claim 2, wherein the fasteners are positioned at substantially opposite ends of the fastening portion on the first coupling element and the corresponding fasteners are positioned at substantially opposite ends of the fastening portion on the second coupling element.

7. The ostomy belt system of claim 1, wherein the outer wall of the ostomy pouch includes a distal side, a proximal side having an inlet opening formed therein, and a barrier extending from the proximal side, wherein the belt coupling element is positioned between the barrier and the proximal side.

8. An ostomy belt comprising:
   a strip of material;
   a first coupling element and a second coupling element configured for releasable engagement with the first coupling element, wherein each of the first and second coupling elements is secured to the strip of material, wherein the first and second coupling elements are configured to form a closed loop having a central opening when engaged together; and
   one or more flexible sections formed on each of the first and second coupling elements to allow for flexing of each coupling element at one or more predetermined locations, wherein the one or more flexible sections are configured to allow the first and second coupling elements to bend or flex with movement of a user and to conform to a contour of a peristomal region of the user, and wherein the one or more flexible sections are formed by one or more of areas or lines of a reduced material thickness, changes in material profile, and two materials having different flexibility properties.

9. The ostomy belt of claim 8, wherein the first coupling element and second coupling element each include a base secured to the strip of material and a fastening portion extending from the base, wherein the first coupling element includes one or more fasteners and the second coupling element includes one or more corresponding fasteners configured to releasably engage respective fasteners of the first coupling element.

10. The ostomy belt of claim 9, wherein the respective fastening portions form open, curved sections.

11. The ostomy belt of claim 9, wherein the fasteners are positioned at substantially opposite ends of the fastening portion on the first coupling element and the corresponding fasteners are positioned at substantially opposite ends of the fastening portion on the second coupling element.

12. The ostomy belt of claim 9, wherein the base includes an opening for receiving the strip of material, wherein the ostomy belt is configured as an adjustable belt including a sliding buckle.

* * * * *